(12) United States Patent
Maa et al.

(10) Patent No.: US 12,251,572 B2
(45) Date of Patent: Mar. 18, 2025

(54) THERAPEUTIC LIGHTING APPARATUS

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 244 days.

(21) Appl. No.: 18/129,027

(22) Filed: Mar. 30, 2023

(65) Prior Publication Data

US 2023/0233873 A1 Jul. 27, 2023

Related U.S. Application Data

(63) Continuation-in-part of application No. 18/101,569, filed on Jan. 25, 2023, now Pat. No. 12,127,314, which is a continuation-in-part of application No. 17/981,123, filed on Nov. 4, 2022, now Pat. No. 12,048,078, which is a continuation-in-part of application No. 17/509,877, filed on Oct. 25, 2021, now abandoned, which is a continuation-in-part of (Continued)

(51) Int. Cl.
*A61N 5/06* (2006.01)

(52) U.S. Cl.
CPC .... *A61N 5/0622* (2013.01); *A61N 2005/0651* (2013.01); *A61N 2005/0659* (2013.01); *A61N 2005/0663* (2013.01)

(58) Field of Classification Search
CPC .......... A61N 2/002; A61N 2/006; A61N 2/02; A61N 2005/0602; A61N 2005/0605; A61N 2005/0606; A61N 2005/0607; A61N 2005/0608; A61N 2005/061; A61N 2005/0611; A61N 2005/0612; A61N 2005/0626; A61N 2005/0637; A61N 2005/0642; A61N 2005/0645; A61N 2005/0647; A61N 2005/0648; A61N 2005/0659; A61N 2005/0661; A61N 2005/0663; A61N 5/0603; A61N 5/0618; A61N 5/062; A61N 5/0622; A61N 5/0624; A61N 5/06; A61N 2005/0662; H05B 45/20; H05B 41/34

See application file for complete search history.

(56) References Cited

U.S. PATENT DOCUMENTS

2019/0076670 A1* 3/2019 Vyshedskiy ............ G16H 20/70
2021/0393977 A1* 12/2021 Nuytkens ............ A61N 5/0618

(Continued)

*Primary Examiner* — Monica C King

(74) *Attorney, Agent, or Firm* — Andy M. Han; Han IP PLLC

(57) ABSTRACT

A therapeutic lighting apparatus includes two white light sources each with a different color temperature and a controller. The controller operates the lighting apparatus in either a color temperature fusion mode or a color temperature flickering mode or both simultaneously such that the color temperature flickering mode can be used for treating a patient with Alzheimer's disease. The lighting apparatus can be enhanced with a green light source for supporting a green light mode for treating migraine headache. Similarly, the lighting apparatus can be enhanced with a red light source for supporting a red light mode for tissue repairing. Alternatively, the lighting apparatus can be enhanced with a near-infrared (IR) radiation source for supporting a near-IR mode for lowering the heartbeat, uplifting the mood, and improving the immunization system of a subject.

9 Claims, 2 Drawing Sheets

Related U.S. Application Data application No. 17/148,277, filed on Jan. 13, 2021, now Pat. No. 11,191,863, which is a continuation-in-part of application No. 17/094,567, filed on Nov. 10, 2020, now Pat. No. 11,103,612, which is a continuation-in-part of application No. 16/180,416, filed on Nov. 5, 2018, now Pat. No. 10,874,762.

(56) References Cited

U.S. PATENT DOCUMENTS

| | | | |
|---|---|---|---|
| 2022/0280807 A1* | 9/2022 | van de Ven | A61N 5/0618 |
| 2024/0431010 A1* | 12/2024 | Yan | H05B 45/20 |

* cited by examiner

THERAPEUTIC LIGHTING APPARATUS

CROSS REFERENCE TO RELATED PATENT APPLICATIONS

The present disclosure is a continuation-in-part (CIP) of U.S. patent application Ser. No. 18/101,569, filed 23 Jan. 2023. Content of aforementioned application is herein incorporated by reference in its entirety.

BACKGROUND

Technical Field

The present disclosure pertains to the field of lighting apparatus and, more specifically, proposes a therapeutic lighting apparatus for treating Alzheimer's disease or migraine, or boosting general health of a subject.

Description of Related Art

In U.S. patent application Ser. No. 18/101,569, a lighting apparatus that flickers between two white light sources each with a different color temperature was introduced for treating Alzheimer's disease. Recently, it has been discovered that exposing migraine patents to green light, 20% of the patents showed improvement on their migraine headache (e.g., Martin et al., Cephalalgia 2021, Vol. 41(2) 135-147, https://pubmed.ncbi.nlm.nih.gov/32903062/). This leads to the idea of augmenting the lighting apparatus described in U.S. patent application Ser. No. 18/101,569 with a green light source such that the same lighting apparatus can be used for treating both Alzheimer and migraine patients. Similarly, red light therapy is well known and widely used for tissue repair. It is reasonable to augment the lighting apparatus described in U.S. patent application Ser. No. 18/101,569 with a red light source such that the same lighting apparatus can be used for both Alzheimer treatment and tissue repair.

Another study published in https://www.mdpi.com/2079-7737/12/1/60 by M. Glimenez et al. demonstrates the use of near-infrared (IR) on test subjects with the results of immediate and lasting impact on lowering heartbeat, uplifting the mood, and improving the immunization system. It would make sense to incorporate a near-IR light source in the lighting apparatus described in U.S. patent application Ser. No. 18/101,569 for treating Alzheimer and for boosting general health of a subject.

The following terms are defined below (slightly different from the definitions used in U.S. patent application Ser. No. 18/101,569) and will be used later in the disclosure:

Color temperature fusion refers to the mixing of two white light sources each with a different color temperature wherein the two light sources are on simultaneously.

Color temperature flickering refers to the flicking of two white light sources each with a different color temperature wherein the two light sources are on alternately.

SUMMARY

In one aspect of the present disclosure, the therapeutic lighting apparatus comprises a first white light source with a first color temperature, a second white light source with a second color temperature, different from the first color temperature, and a controller. The controller is configured to operate the lighting apparatus in at least two of the three operational modes comprising a color temperature fusion mode, a color temperature flickering mode, and a combo mode. In the color temperature fusion mode, the controller is configured to mix a combination ratio of the first white light source and the second white light source. In the color temperature flickering mode, the controller is configured to turn on the first white light source and the second white light source alternately at a frequency between 35 Hz and 45 Hz. The color temperature flickering mode is used for treating Alzheimer's disease. In the combo mode, the controller is configured to operate the color temperature fusion and the color temperature flickering simultaneously. In the combo mode, the controller first creates two combinations of the first white light source and the second white light source to produce two fused color temperatures, and then followed by flickering between these two fused color temperatures, thus yielding a third fused color temperature approximating the average of two fused color temperatures.

It is noted that the disclosure introduced in U.S. patent application Ser. No. 18/101,569 requires the flickering of two different color temperatures. In other words, it supports the color temperature flickering mode and the combo mode where two different color temperatures are fused first and then flickered. However, the disclosure introduced in U.S. patent application Ser. No. 18/101,569 is not required to support the color temperature fusion mode. The lighting apparatus of the present disclosure supports at least two of the three modes: the color temperature fusion mode, the color temperature flickering mode, and the combo mode. It is thus different from, but inclusive of, the lighting apparatus described in U.S. patent application Ser. No. 18/101,569.

In some embodiments, the first white light source comprises a white light emitting diode (LED) and the second white light source comprises a white LED. LED is a light source that can be turned on and off instantly, and thus is suitable for color temperature flickering operation.

In some embodiments, the controller is configured to tune the color temperature of the lighting apparatus in either the color temperature fusion mode or the combo mode or both, thus achieving color tuning. The controller changes the color temperature in the color temperature fusion mode by changing the combination ratio of the first white light source and the second white light source. The controller changes the color temperature in the combo mode by firstly tuning two fused color temperatures (again by changing the combination ratios of the first white light source and the second white light source) and then followed by flickering between these two fused color temperatures, thus yielding a third fused color temperature approximating the average of these two fused color temperatures.

In some embodiments, the lighting apparatus further comprises a green light source. The controller is configured to operate the lighting apparatus in an additional mode, the green light mode. During such mode the controller turns on the green light source for treating migraine headache. It is noted that the color temperature fusion mode, the color temperature flickering mode, and the green light mode are not mutually exclusive, and the combo mode may as well be enhanced to have all three of these modes operating simultaneously. In some embodiments, the green light source comprises a green LED.

In some embodiments, the lighting apparatus further comprises a red light source. The controller is configured to operate the lighting apparatus in an additional mode, the red light mode. During such mode the controller turns on the red light source for tissue repairing. It is noted that the color temperature fusion mode, the color temperature flickering mode, and the red light mode are not mutually exclusive, and the combo mode may as well be enhanced to have all three of these modes operating simultaneously. In the red light mode, the controller may turn on the red light source continuously or in a pulsed manner, depending on the red light therapy recommendation. In some embodiments, the red light source comprises a red LED.

In some embodiments, the lighting apparatus further comprises a near-IR radiation source. The controller is configured to operate the lighting apparatus in an additional mode, the near-IR mode. During such mode the controller turns on the near-IR radiation source for boosting the general health of a subject, e.g., lowering the heartbeat, uplifting the mood, and improving the immunization system of the subject. It is noted that the color temperature fusion mode, the color temperature flickering mode, and the near-IR mode are not mutually exclusive, and the combo mode may as well be enhanced to have all three of these modes operating simultaneously. In the near-IR mode, the controller may turn on the near-IR radiation source continuously or in a pulsed manner, depending on the near-IR therapy recommendation. In some embodiments, the near-IR radiation source comprises a near-IR LED.

BRIEF DESCRIPTION OF THE DRAWINGS

The accompanying drawings are included to aid further understanding of the present disclosure and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of therapeutic lighting apparatuses having different form factors.

The present disclosure discloses a therapeutic lighting apparatus includes two white light sources each with a different color temperature and a controller. The controller operates the lighting apparatus in either a color temperature fusion mode or a color temperature flickering mode or both simultaneously such that the color temperature flickering mode can be used for treating a patient with Alzheimer's disease. The lighting apparatus can be enhanced with a green light source for supporting a green light mode for treating migraine headache. Similarly, the lighting apparatus can be enhanced with a red light source for supporting a red light mode for tissue repairing. Alternatively, the lighting apparatus can be enhanced with a near-infrared (IR) radiation source for supporting a near-IR mode for lowering the heartbeat, uplifting the mood, and improving the immunization system of a subject.

EXAMPLE IMPLEMENTATIONS

Figure 1:
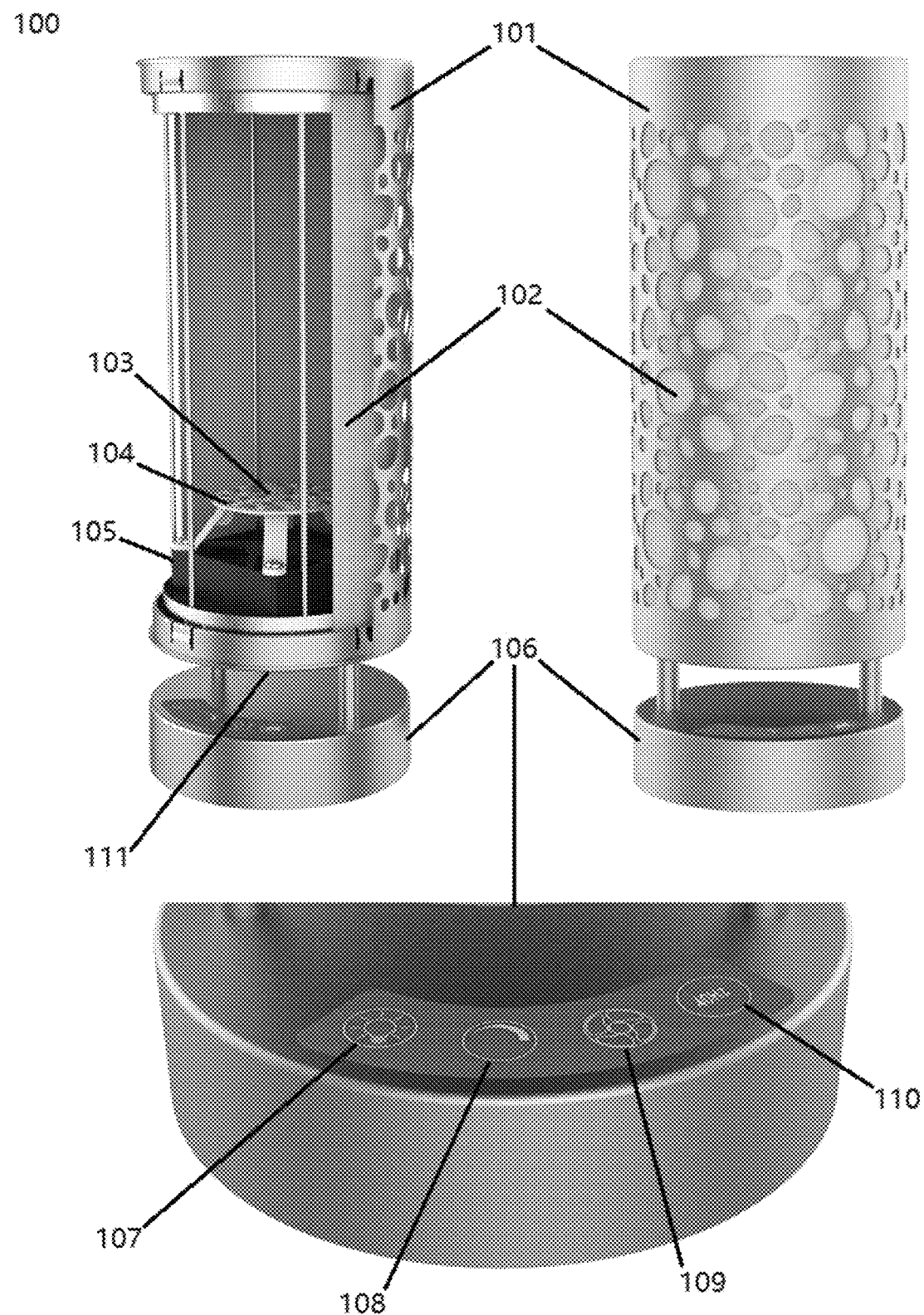
FIG. 1 schematically depicts a first embodiment of the present disclosure.

FIG. 1 is an embodiment of the therapeutic lighting device of the present disclosure in a form of a desktop lamp 100 under a proposed scheme in accordance with the present disclosure. The desktop lamp 100 has an external housing 101 to house an air filter 102, a fan 105, and two types of LEDs: 3000K white LEDs 104 and 5000K white LEDs 103. The controller is hidden inside the base 106 and is configured to provide various functions: color selection (via touch button 107), bi-level dimming (via touch button 108), fan operation 109 (via touch button 109), and 40 Hz flickering operation (via touch button 110).

The color selection button 107 is used to set the color temperature of the lamp. In some implementations, there are three color temperature modes under normal operation as follows:
  Color Warm: only 3000K white LEDs 104 are turned on.
  Color Medium: 3000K white LEDs 104 and 5000K white LEDs 103 are mixed to create 4000K light.
  Color Cold: only 5000K white LEDs 103 are turned on.
  In the Color Medium mode, the controller performs a color temperature fusion of the 3000K LEDs and the 5000K LEDs with 50% light output from each (presuming 3000K LEDs and 5000K LEDs consuming the same amount of energy with a similar efficacy).

When the 40 Hz flickering button 110 is triggered for Alzheimer's disease treatment, there are also three other color temperature modes supported by the color selection button 107:
  Color Warm: flickering between 3000K and 3200K color temperatures at 40 Hz for creating a blended light at 3100K, wherein 3200K color temperature is created by a color temperature fusion of 90% 3000K LEDs and 10% 5000K LEDs.
  Color Medium: flickering between 3900K and 4100K color temperatures at 40 Hz for creating a blended light at 4000K, wherein 3900K temperature is created by a color temperature fusion of 55% 3000K LEDs and 45% 5000K LEDs, and 4100K color temperature is create by a color temperature fusion of 45% 3000K LEDs and 55% 5000K LEDs.
  Color Cold: flickering between 4800K and 5900K color temperatures at 40 Hz for creating a blended light at 4900K, wherein 4800K color temperature is created by a color temperature fusion of 10% 3000K LEDs and 90% 5000K LEDs.

It can be seen under the 40 Hz flickering operation, in the Color Warn, the Color Medium, and the Color Cold modes, the controller performs color temperature fusion first on the 3000K LEDs 104 and the 5000K LEDs 103, and then followed by color temperature flickering, i.e., a combo mode operation of 3000K LEDs and the 5000K LEDs. This is a good example showing that color temperature fusion and color temperature flickering are not mutually exclusive.

Figure 2:
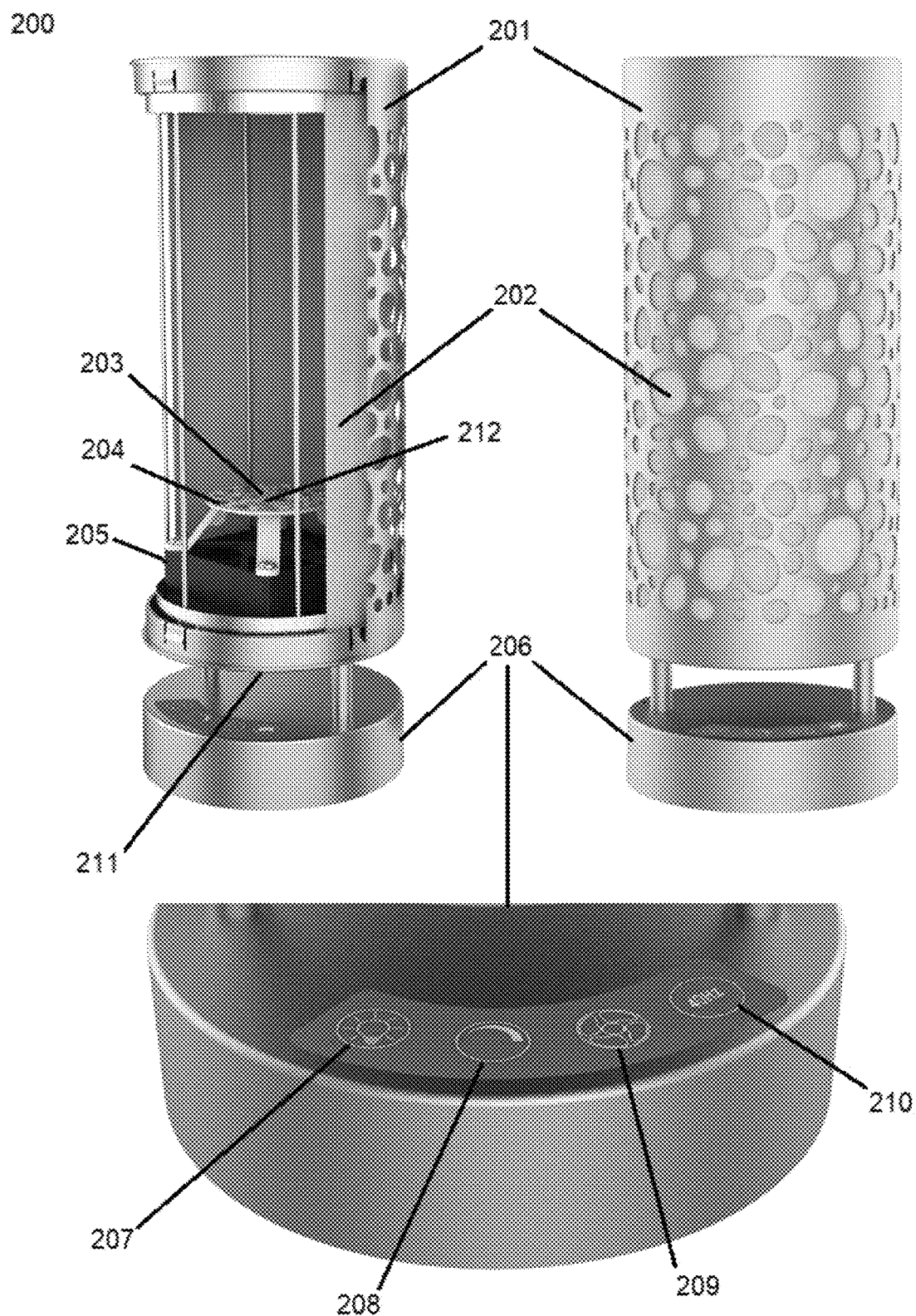
FIG. 2 schematically depicts a second embodiment of the present disclosure with green LEDs.

FIG. 2 is an embodiment of the therapeutic lighting device of the present disclosure in a form of a desktop lamp 200 under another proposed scheme in accordance with the present disclosure. The desktop lamp 200 has an external housing 201 to house an air filter 202, a fan 205, and three types of LEDs: 3000K white LEDs 204, 5000K white LEDs 203, and 530 nm green LEDs 212. The controller is hidden inside the base 206 and is configured to provide various functions: color selection (via touch button 207), bi-level dimming (via touch button 208), fan operation 209 (via touch button 209), and 40 Hz flickering operation (via touch button 120).

The color selection button 207 is used to set the color temperature of the lamp. In some implementations, there are four color temperature modes under normal operation:

Color Warm: only 3000K white LEDs 204 are turned on.
Color Medium: 3000K white LEDs 204 and 5000K white LEDs 203 are mixed to create 4000K light.
Color Cold: only 5000K white LEDs 203 are turned on.
Color Green: only 530 nm green LEDs 212 are turned on (for migraine treatment).

In the Color Medium mode, the controller performs a color temperature fusion of the 3000K LEDs and the 5000K LEDs with 50% light output from each (presuming 3000K LEDs and 5000K LEDs consuming the same amount of energy with a similar efficacy).

When the 40 Hz flickering button 210 is triggered for Alzheimer's disease treatment, there are also four color temperature modes supported by the color selection button 207:

Color Warm: flickering between 3000K and 3200K color temperatures at 40 Hz for creating a blended light at 3100K, wherein 3200K color temperature is created by a color temperature fusion of 90% 3000K LEDs and 10% 5000K LEDs.
Color Medium: flickering between 3900K and 4100K color temperatures at 40 Hz for creating a blended light at 4000K, wherein 3900K temperature is created by a color temperature fusion of 55% 3000K LEDs and 45% 5000K LEDs, and 4100K color temperature is create by a color temperature fusion of 45% 3000K LEDs and 55% 5000K LEDs.
Color Cold: flickering between 4800K and 5900K color temperatures at 40 Hz for creating a blended light at 4900K, wherein 4800K color temperature is created by a color temperature fusion of 10% 3000K LEDs and 90% 5000K LEDs.
Color Green: turning on 530 nm green LEDs 212 at 40 Hz (for migraine treatment).

In the Color Green mode under 40 Hz flickering operation, the flickering green light can be used to treat both migraine and Alzheimer's disease. However, turning on/off a green light at 40 Hz may create discomfort to human eyes. It is foreseeable to flicker two similar but different green light sources at 40 Hz, rather than turning on/off a single green light source at 40 Hz, thus providing a more comfortable color temperature flickering of these two green light sources for treating migraine and Alzheimer's disease simultaneously.

The control panel of the embodiment 200 can be augmented by adding another button for turning on/off green LEDs 212 such that the color selection button 207 would only support three color temperature modes: Color Warm, Color Medium, and Color Cold. The addition of a separate on/off button for green LEDs 212 can then support the turning on of both white LEDs 204, 203 and green LEDs 212 simultaneously.

The green LEDs 212 may be replaced with some red LEDs for another embodiment that supports a red light mode. In the red light mode, the (hidden) controller turns on the red LEDs for tissue repair. The red light mode may be controlled by the color selection button 207. Alternatively, the on/off of the red LEDs may be controlled by another control button, thus affording the turning on of white LEDs 204, 203 and red LEDs simultaneously.

The green LEDs 212 may be replaced with some near-IR LEDs for yet another embodiment that supports a near-IR mode. In the near-IR mode, the (hidden) controller turns on the near-IR LEDs for a general health booth of a subject by lowering the heartbeat, uplifting the mood, and improving the immunization system of the subject. The near-IR mode may be controlled by the color selection button 207. Alternatively, the on/off of near-IR LEDs may be controlled by another control button, thus affording the turning on of white LEDs 204, 203 and the near-IR LEDs simultaneously.

Additional and Alternative Implementation Notes

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A therapeutic lighting apparatus, comprising:
a first white light source configured to emit a first white light with a first color temperature;
a second white light source configured to emit a second white light with a second color temperature different from the first color temperature; and
a controller,
wherein:
the controller is configured to operate the lighting apparatus in at least two of three operational modes comprising a color temperature fusion mode, a color temperature flickering mode, and a combo mode such that:
in the color temperature fusion mode, the controller is configured to mix a combination ratio of the first white light and the second white light,
in the color temperature flickering mode, the controller is configured to turn on the first white light source and the second white light source alternately at a frequency between 35 Hz and 45 Hz, and
in the combo mode, the controller is configured to operate in the color temperature fusion mode and the color temperature flickering mode simultaneously.

2. The therapeutic lighting apparatus of claim 1, wherein the first white light source comprises a first white light emitting diode (LED), and wherein the second white light source comprises a second white LED.

3. The therapeutic lighting apparatus of claim 1, wherein the controller is configured to tune a color temperature of the lighting apparatus in either the color temperature fusion mode or the combo mode, or both.

4. The therapeutic lighting apparatus of claim 1, further comprising:
   a green light source,
      wherein the controller is further configured to operate the lighting apparatus in a green light mode in which the controller turns on the green light source.

5. The therapeutic lighting apparatus of claim 4, wherein the green light source comprises a green light emitting diode (LED).

6. The therapeutic lighting apparatus of claim 1, further comprising:
   a red light source,
      wherein the controller is further configured to operate the lighting apparatus in a red light mode in which the controller turns on the red light source.

7. The therapeutic lighting apparatus of claim 1, wherein the red light source comprises a red light emitting diode (LED).

8. The therapeutic lighting apparatus of claim 1, further comprising:
   a near-infrared (IR) radiation source configured to emit an IR light at a wavelength in a range of 760 nm~1400 nnm,
   wherein the controller is configured to operate the lighting apparatus in a near-IR mode in which the controller turns on the near-IR radiation source.

9. The therapeutic lighting apparatus of claim 8, wherein the near-IR light source comprises a near-IR light emitting diode (LED).

* * * * *